United States Patent [19]

Nappa et al.

[11] Patent Number: 5,396,000
[45] Date of Patent: Mar. 7, 1995

[54] PROCESS FOR THE MANUFACTURE OF 1,1,1,2,3,-PENTAFLUOROPROPANE

[75] Inventors: Mario J. Nappa, Newark; V.N. Mallikarjuna Rao, Wilmington, both of Del.

[73] Assignee: E. I. Du Pont de Nemours and Company, Wilmington, Del.

[21] Appl. No.: 66,451

[22] Filed: May 24, 1993

[51] Int. Cl.$^6$ .................... C07C 19/08; C07C 17/34
[52] U.S. Cl. ........................ 870/175; 570/156; 570/157
[58] Field of Search ............ 570/156, 175, 176, 159

[56] References Cited

U.S. PATENT DOCUMENTS

| | | | |
|---|---|---|---|
| 3,432,562 | 3/1969 | Gardner | 260/653.5 |
| 4,766,260 | 8/1988 | Manzer et al. | 570/168 |
| 4,902,838 | 2/1990 | Manzer et al. | 570/156 |
| 5,059,729 | 10/1991 | Gervasutti | 570/175 |
| 5,068,473 | 11/1991 | Kellner et al. | 570/176 |
| 5,136,113 | 8/1992 | Rao | 570/176 |

FOREIGN PATENT DOCUMENTS

| | | | |
|---|---|---|---|
| 491825 | 4/1953 | Canada | 570/156 |
| 704720 | 3/1965 | Canada | 570/156 |
| 1191192 | 5/1970 | United Kingdom | 570/156 |
| 9008748 | 8/1990 | WIPO | 570/176 |
| 93/02150 | 2/1993 | WIPO | C09K 5/04 |
| WO93/25510 | 12/1993 | WIPO | |

OTHER PUBLICATIONS

Abstract re CA 117(6): 49948p and DD 298419(1992).
Abstract re EP 162746(1984).
Abstract re JP 02272086(1990).
Abstract re CA 114(14): 125031q and JP 02272086(1990).
Abstract re CA 114(10): 83236c and DE 3903336(1990).
Knunyants et al., *Izvest. Akad, Nauk. S.S.S.R, Otdel. Khim. Nauk.* pp. 1312–1317 (1960).

*Primary Examiner*—Alan Siegel

[57] ABSTRACT

A process is disclosed for producing $CF_3CHFCH_2F$ using vapor phase catalytic dehydrohalogenation to produce $CF_3CF=CHF$ and HF, followed by vapor phase catalytic hydrogenation of $CF_3CF=CHF$ in the presence of HF.

15 Claims, No Drawings

PROCESS FOR THE MANUFACTURE OF 1,1,1,2,3,-PENTAFLUOROPROPANE

FIELD OF THE INVENTION

This invention relates to a process for producing fluorine-substituted hydrocarbons, and more particularly to a process for producing 1,1,1,2,3-pentafluoropropane.

BACKGROUND

There has been recent concern that completely halogenated chlorofluorocarbons might be detrimental toward the Earth's ozone layer. Consequently, there is a world-wide effort to use halogen-substituted hydrocarbons which contain fewer chlorine substituents. For example, 1,1,1,2-tetrafluoroethane (HFC-134a), a hydrofluorocarbon having zero ozone depletion potential, is being considered as a replacement for dichlorodifluoromethane (CFC-12) in refrigeration systems. The production of hydrofluorocarbons (i.e., compounds containing only carbon, hydrogen and fluorine), has been the subject of renewed interest to provide environmentally desirable products for use as solvents, blowing agents, refrigerants, cleaning agents, aerosol propellants, heat transfer media, dielectrics, fire extinguishants and power cycle working fluids (see, e.g., PCT International Publication No. WO93/02150).

SUMMARY OF THE INVENTION

A process is provided in accordance with this invention for producing the hydrofluorocarbon $CF_3CHFCH_2F$. The process comprises the steps of dehydrohalogenating $CF_3CHFCHF_2$ at an elevated temperature in the vapor phase over a catalyst selected from the group consisting of aluminum fluoride, fluorided alumina, metal supported on aluminum fluoride, metal supported on fluorided alumina, and mixtures thereof, to produce a product containing $CF_3CF=CHF$ and HF; and reacting said $CF_3CF=CHF$ in the vapor phase with hydrogen over a hydrogenation catalyst in the presence of HF to produce $CF_3CHFCH_2F$.

DETAILED DESCRIPTION

This invention provides a process for producing 1,1,1,2,3-pentafluoropropane (i.e., $CF_3CHFCH_2F$ or HFC-245eb) using 1,1,1,2,3,3-hexafluoropropane (i.e., $CF_3CHFCHF_2$ or HFC-236ea).

In accordance with this invention, $CF_3CHFCHF_2$ is dehydrofluorinated to $CF_3CF=CHF$ over a catalyst comprising aluminum fluoride or fluorided alumina. Suitable catalysts which may be used for the dehydrofluorination include fluorided alumina, aluminum fluoride, metals on aluminum fluoride, and metals on fluorided alumina. Fluorided alumina and aluminum fluoride can be prepared as described in U.S. Pat. No. 4,902,838. Suitable metals include chromium, magnesium (e.g., magnesium fluoride), Group VIIB metals (e.g., manganese), Group IIIB metals (e.g., lanthanum), and zinc. In use, such metals are normally present as halides (e.g., fluorides), as oxides and/or as oxyhalides. Metals on aluminum fluoride and metals on fluorided alumina can be prepared by procedures described in U.S. Pat. No. 4,766,260. Preferably, when supported metals are used, the total metal content of the catalyst is from about 0.1 to 20 percent by weight, typically from about 0.1 to 10 percent by weight. Preferred catalysts include catalysts consisting essentially of aluminum fluoride and/or fluorided alumina.

The catalytic dehydrofluorination of $CF_3CHFCHF_2$ is suitably conducted at a temperature in the range of from about 300° C. to about 450° C., preferably from about 375° C. to about 425° C., and most preferably from about 400° C. to about 415° C. The contact time is typically from about 1 to about 450 seconds, preferably from about 200 to about 300 seconds.

The effluent from the dehydrofluorination contains $CF_3CF=CHF$, HF and typically other compounds such as unreacted $CF_3CHFCHF_2$.

In accordance with this invention, $CF_3CF=CHF$ produced by the catalytic dehydrofluorination of $CF_3CHFCHF_2$ is contacted with hydrogen in the presence of a hydrogenation catalyst and in the presence of HF. $CF_3CF=CHF$ may be isolated from the dehydrofluorination reaction effluent by distillation if desired, and HF may then be separately added in the hydrogenation step. However, it is preferred to pass the HF from the dehydrofluorination, and more preferably the entire effluent from the dehydrofluorination of $CF_3CHFCHF_2$ (including the HF), with hydrogen over the hydrogenation catalyst. While the hydrogenation reaction proceeds even in the absence of HF, the HF present during the hydrogenation step moderates the hydrogenation reaction. In any case, in accordance with this invention, $CF_3CHFCH_2F$ may be produced from $CF_3CHFCHF_2$ without separation and removal of HF prior to $CF_3CHFCH_2F$ production. In addition, passing the entire effluent from the dehydrofluorination step onto the hydrogenation avoids handling concerns associated with olefinic halogenated compounds as well as HF. The HF of the hydrogenation effluent is available for use along with other compounds thereof. For example, the HF is available for azeotropic combination with the fluorinated hydrocarbon compounds of the effluent from the hydrogenation reaction.

The reaction of $CF_3CF=CHF$ with hydrogen in the presence of HF employs a hydrogenation catalyst. Normally, the hydrogenation catalyst contains a metal (e.g, a Group VIII metal or rhenium). The metal may be supported (e.g., Pd supported on alumina, aluminum fluoride, or carbon) or may be unsupported (e.g., Raney nickel). Carbon-supported metal catalysts are preferred, with Pd/C being particularly preferred. The carbon support is preferably washed with acid prior to depositing the metal on it. Procedures for preparing a catalyst of Group VIII metal or rhenium on an acid-washed carbon support are disclosed in U.S. Pat. No. 5,136,113, the entire contents of which are hereby incorporated by reference.

The contact of $CF_3CF=CHF$ with hydrogen in the presence of a hydrogenation catalyst and HF is suitably conducted at a temperature in the range of from about 50° C. to about 300° C., and preferably from about 50° C. to about 200° C. Contact time is typically from about 5 to 100 seconds, preferably about 10 to 30 seconds.

The molar ratio of hydrogen to $CF_3CF=CHF$ typically is in the range from about 1:1 to about 50:1, and is preferably from about 1.5:1 to about 25:1, and more preferably from about 2:1 to about 10:1. Normally, at least about 100 ppm HF is present; and typically the HF is approximately stoichiometric with $CF_3CF=CHF$, especially when the entire effluent from the dehydrofluorination step is passed to the hydrogenation step.

Hydrogen can be fed either in the pure state or diluted with inert gas (e.g., nitrogen, helium or argon).

The reaction products from the hydrogenation may be separated by conventional techniques, such as distillation. $CF_3CHFCH_2F$ likely forms an azeotrope with HF; and conventional decantation/distillation may be employed if further purification of $CF_3CHFCH_2F$ is desired.

Pressure is not critical for either the hydrogenation or dehydrofluorination steps. Atmospheric and superatmospheric pressures (e.g., pressure from about 100 kPa to 7000 kPa) are the most convenient and are therefore preferred.

The hydrogenation and dehydrofluorination reactions may be conducted in any suitable reactor, including fixed and fluidized bed reactors. The reaction vessel should be constructed from materials which are resistant to the corrosive effects of hydrogen fluoride such as Inconel ™ nickel alloy and Hastelloy ™ nickel alloy.

The $CF_3CHFCHF_2$ used as a reactant in this process may be readily produced from hexafluoropropylene. Hexafluoropropylene may, for example, be advantageously contacted with hydrogen over a hydrogenation catalyst such as those described above (e.g., Pd/alumina) to produce 1,1,1,2,3,3-hexafluoropropane, see Knunyants et al., Izvest. Akad. Nauk. S.S.S.R, Otdel. Khim. Nauk. (Eng. Translation), pp. 1312–1317 (1960).

$CF_3CHFCH_2F$ has numerous uses including applications in compositions used as refrigerants, blowing agents, propellants, cleaning agents, and heat transfer agents.

Practice of the invention will become further apparent from the following non-limiting examples.

EXAMPLE 1

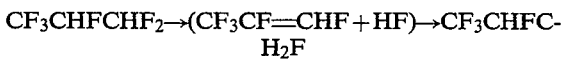

A 15 in (38.1 cm) × ⅜ in (0.95 cm) Hastelloy ™ nickel alloy tube was filled with 9.52 g (about 13 mL) $AlF_3 \cdot 3 H_2O$ ground to 12/20 mesh (1.68/0.84 mm).

A. Catalyst Activation (1st Reactor)

The catalyst was activated by heating at 350° C. for 3 hours under a nitrogen purge (50 sccm, $8.4 \times 10^{-7}$ m³/s).

B. Reaction: $CF_3CHFCHF_2 \rightarrow CF_3CF = CHF + HF$

The reactor was heated to 410°–440° C. The flow of 1,1,1,2,3,3-hexafluoropropane (3.0 sccm, $5.0 \times 10^{-8}$ m³/s) was begun to the reactor. The effluent of this reactor which contained 1,2,3,3,3-pentafluoropropene (HFC-1225ey) and HF was passed directly into the next reactor.

C. Hydrogenation of HFC-1225ey

One inch (2.54 cm) Monel ™ nickel alloy compression fittings were used as a reactor (1.91 cm × 6.99 cm internal cavity dimensions). This reactor was filled with 0.5% Pd on acid-washed carbon (5.41 g, 15 mL). The reactor was heated to 153° C. and the reactor effluent (including both $CF_3CF = CHF$ and HF) from B described above (dehydrofluorination of $CF_3CHFCHF_2$) was introduced into the reactor. With this was added 30 sccm ($5.0 \times 10^{-7}$ m³/s) $H_2$. The gaseous products from this reaction analyzed as: $CF_3CHFCF_3$ (HFC-227ea), 0.2%; $CF_3CF = CHF$ (HFC-1225ey), 0.1%; $CF_3CHFCHF_2$ (HFC-236ea), 6.3%; $CF_3CHFCH_3$ (HFC-254eb), 7.2%; $CF_3CHFCH_2F$ (HFC-245eb), 85.3%.

This corresponds to a 94% conversion and 91% selectivity for HFC-245eb from HFC-236ea.

EXAMPLE 2

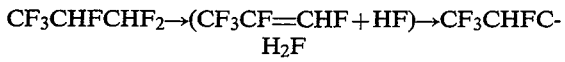

A 15 in (38.1 cm) × ⅜ in (0.95 cm) Hastelloy ™ nickel alloy tube was filled with 8.44 g (about 13 mL) gamma-alumina ground to 12/20 mesh (1.68/0.84 mm).

A. Catalyst Activation (1st Reactor)

The gamma-alumina catalyst was activated by heating at 175° C. for 30 min. under a nitrogen purge (25 sccm, $4.2 \times 10^{-7}$ m³/s). HF was fed at 25 sccm ($4.2 \times 10^{-7}$ m³/s) for 85 minutes and a temperature rise to 176° C. was noted. The temperature was raised to 250° C. the HF flow increased to 40 sccm ($6.7 \times 10^{-7}$ m³/s), and the $N_2$ flow decreased to 10 sccm ($1.7 \times 10^{-7}$ m³/s) for 15 hr. and 10 min. The temperature was raised to 350° C. while maintaining flows for 150 minutes, and then the temperature was raised to 450° C. while maintaining flows for 230 minutes.

B. Reaction: $CF_3CHFCHF_2 \rightarrow CF_3CF = CHF + HF$

The reactor was heated to 415° C. The flow of 1,1,1,2,3,3-pentafluoropropane (HFC-236ea) (8.5 sccm, $1.42 \times 10^{-7}$ m³/s) was begun to the reactor. The effluent of this reactor which contained 1,2,3,3,3-pentafluoropropene (HFC-1225ey) and HF was passed directly into the next reactor.

C. Hydrogenation of HFC-1225ey

One inch (2.54 cm) Monel ™ nickel alloy compression fittings were used as a reactor (1.91 cm × 6.99 cm internal cavity dimensions). This reactor was filled with 0.5% Pd on acid-washed carbon (5.61 g, 15 cc). The reactor was heated to 153° C. and the reactor effluent (including both $CF_3CF = CHF + HF$) from B described above (dehydrofluorination of HFC-236ea) was introduced into the reactor. With this was added 45 sccm ($7.5 \times 10^{-7}$ m³/s) $H_2$. The gaseous products from this reaction analyzed as: $CF_3CHFCHF_2$ (HFC-236ea), 3.6%; $CF_3CHFCH_3$ (HFC-254eb), 14.8%; $CF_3CHFCH_2F$ (HFC-245eb), 80.9%. Other trace impurities were also observed. This corresponds to a 96% conversion and 84% selectivity for HFC-245eb from HFC-236ea.

Particular embodiments of the invention are illustrated by the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for producing $CF_3CHFCH_2F$ comprising the steps of:

dehydrohalogenating $CF_3CHFCHF_2$ at an elevated temperature in the vapor phase over a catalyst selected from the group consisting of aluminum fluoride, fluorided alumina, metal on aluminum fluoride, metal on fluorided alumina and mixtures thereof, the metal of said metal aluminum fluoride and metal on fluorided alumina being selected from the group consisting of chromium, magnesium, Group VIIB metals, Group IIIB metals and zinc, to produce a product containing $CF_3CF{=}CHF$ and HF;

adding hydrogen, HF and said $CF_3CF{=}CHF$ to a reaction vessel containing a hydrogenation catalyst; and reacting said $CF_3CF{=}CHF$ in the vapor phase with hydrogen over said hydrogenation catalyst in the presence of HF, to produce $CF_3CHFCH_2F$.

2. The process of claim 1 wherein the effluent from the dehydrohalogenation of $CF_3CHFCHF_2$ is passed with hydrogen over the hydrogenation catalyst.

3. The process of claim 1 or claim 2 wherein the hydrogenation catalyst is a carbon-supported metal catalyst.

4. The process of claim 3 wherein the carbon-supported metal is a Group VIII metal or rhenium.

5. The process of claim 3 wherein the hydrogenation catalyst is a carbon-supported palladium catalyst.

6. The process of claim 3 wherein the dehydrohalogenation catalyst consists essentially of aluminum fluoride and/or fluorided alumina.

7. The process of claim 1 or claim 2 wherein the dehydrohalogenation catalyst consists essentially of aluminum fluoride and/or fluorided alumina.

8. The process of claim 2 wherein the molar ratio of hydrogen to $CF_3CF{=}CHF$ reacted therewith is from about 1:1 to about 50:1.

9. The process of claim 2 wherein the dehydrohalogenation is conducted at a temperature in the range of from about 300° C. to about 450° C.; and wherein the hydrogenation is conducted at a temperature in the range of from about 50° C. to about 300° C.

10. The process of claim 1 wherein $CF_3CHFCHF_2$ is produced by contacting $CF_2{=}CFCF_3$ with hydrogen over a hydrogenation catalyst.

11. A process for producing $CF_3CHFCH_2F$ comprising the steps of:

dehydrohalogenating $CF_3CHFCHF_2$ at an elevated temperature in the vapor phase over a catalyst selected from the group consisting of aluminum fluoride, fluorided alumina, metal on aluminum fluoride, metal on fluorided alumina and mixtures thereof, the metal of said metal on aluminum fluoride and metal on fluorided alumina being selected from the group consisting of chromium, magnesium, Group VIIB metals, Group IIIB metals and zinc, to produce a product containing $CF_3CF{=}CHF$ and HF;

adding hydrogen, HF and said $CF_3CF{=}CHF$ to a reaction vessel containing a hydrogenation catalyst containing a Group VIII metal or rhenium; and reacting said $CF_3CF{=}CHF$ in the vapor phase with hydrogen over said hydrogenation catalyst in the presence of HF, to produce $CF_3CHFCH_2F$.

12. The process of claim 11 wherein the metal of said hydrogenation catalyst is supported on acid-washed carbon.

13. The process of claim 11 wherein $CF_3CF{=}CHF$ is reacted with hydrogen in the presence of palladium supported on acid-washed carbon.

14. A process for producing $CF_3CHFCH_2F$ comprising the steps of:

dehydrohalogenating $CF_3CHFCHF_2$ at an elevated temperature in the vapor phase over a catalyst selected from the group consisting of aluminum fluoride, fluorided alumina, metal on aluminum fluoride, metal on fluorided alumina and mixtures thereof, the metal of said metal on aluminum fluoride and metal on fluorided alumina being selected from the group consisting of chromium, magnesium, Group VIIB metals, Group IIIB metals and zinc, to produce a product containing $CF_3CF{=}CHF$ and HF;

adding hydrogen, HF and said $CF_3CF{=}CHF$ to a reaction vessel containing a hydrogenation catalyst; and reacting said $CF_3CF{=}CHF$ in the vapor phase with hydrogen over said hydrogenation catalyst in the presence of HF which is approximately stoichiometric with the $CF_3CF{=}CHF$ reacted.

15. The process of claim 14 wherein said hydrogenation is in the presence of HF produced during said dehydrohalogenation.

* * * * *